United States Patent
Ryu et al.

(10) Patent No.: US 6,936,146 B2
(45) Date of Patent: Aug. 30, 2005

(54) ELECTROCHEMICAL BIOSENSOR READOUT METER

(75) Inventors: Jun-Oh Ryu, Seoul (KR); Jin-Woo Lee, Kyunggi-do (KR); In-Hwan Choi, Kyunggi-do (KR)

(73) Assignee: Allmedicus Co., LTD, Kyunggi-Do (KR)

( * ) Notice: Subject to any disclaimer, the term of this patent is extended or adjusted under 35 U.S.C. 154(b) by 214 days.

(21) Appl. No.: 10/239,120

(22) PCT Filed: Jan. 30, 2001

(86) PCT No.: PCT/KR01/00120

§ 371 (c)(1),
(2), (4) Date: Sep. 19, 2002

(87) PCT Pub. No.: WO01/71329

PCT Pub. Date: Sep. 27, 2001

(65) Prior Publication Data

US 2003/0019750 A1 Jan. 30, 2003

(30) Foreign Application Priority Data

Mar. 22, 2000 (KR) ........................................ 2000-14424

(51) Int. Cl.[7] ..................... G01N 27/416; G01N 27/327
(52) U.S. Cl. .................... 204/406; 204/403.01
(58) Field of Search ................ 204/402, 406, 204/403.01, 403.14

(56) References Cited

U.S. PATENT DOCUMENTS

| | | |
|---|---|---|
| 4,940,945 A | 7/1990 | Littlejohn et al. |
| 4,999,582 A | 3/1991 | Parks et al. |
| 5,352,351 A | 10/1994 | White et al. |
| 5,366,609 A | 11/1994 | White et al. |
| 5,438,271 A | 8/1995 | White et al. |
| 5,653,863 A * | 8/1997 | Genshaw et al. ........ 205/777.5 |
| 5,858,186 A | 1/1999 | Glass |

FOREIGN PATENT DOCUMENTS

| | | |
|---|---|---|
| EP | 0414388 B1 | 9/1993 |
| EP | 1067384 B1 | 1/2001 |
| JP | 1-15649 A | 1/1989 |
| JP | 2-6733 A | 1/1990 |
| JP | 3-156358 A | 7/1991 |

OTHER PUBLICATIONS

Stuart Ball, "Analog–to–Digital Converters," published May 1, 2001, downloaded on Aug. 22, 2004 from www.embedded.com/shared/printableArticle.jhtml?articleID=12801571.*

* cited by examiner

Primary Examiner—Alex Noguerola
(74) Attorney, Agent, or Firm—Timothy J Keefer; Seyfarth Shaw LLP

(57) ABSTRACT

An Electrochemical biosensor readout meter which can do selectively quantitative analysis of sample of living body such as blood sugar, cholesterol and other elements in blood is disclosed. It is an object of this invention to provide electrochemical biosensor readout meter which has no distortion in peak current and can be manufactured in a low cost. In a preferred embodiment of present invention, a voltage converting means (OP2) is set to convert peak current which occurs at $3^{rd}$ voltage applying time (t3) into voltage with no distortion and an amplifier (OP3) is set to make digital voltage signal at measuring time (t4) lower than reference voltage of A/D converter.

6 Claims, 6 Drawing Sheets

PRIOR ART

ELECTROCHEMICAL BIOSENSOR READOUT METER

This application is the national stage under 35 U.S.C. 371 of PCT/KR01/00120, filed on Jan. 30, 2001 and claims priority under 35 U.S.C. 119(a)–(d) from KR 2000-14424, filed on Mar. 22, 2000.

TECHNICAL FIELD

The present invention relates to an electrochemical biosensor readout meter which can operate quantitative analysis on specific biomaterials such as blood sugar, cholesterol and so forth.

BACKGROUND ART

Recently electrochemical biosensors are frequently used in medical field to analyze biomaterials including blood. Among those, enzyme-utilizing electrochemical biosensors are used most generally in hospitals and clinical labs because they are easy to apply, superior in measurement sensitivity, and allow rapid acquisition of test results. Enzyme analyzing method applied in electrochemical biosensors can be largely divided into chromophoric method which is a spectroscopic way and electrode method, an electrochemical way. Generally, the measuring time in chromophoric method takes longer than electrode method, and difficult to analyze significant biomaterials due to the measurement errors caused by the turbidity of biomaterials. Therefore, an electrode method is extensively applied in electrochemical biosensors recently. According to the method, in an electrode system established by screen printing, the quantitative measurement of a material of interest can be achieved by fixing a reagent onto the electrodes, introducing a sample, and applying an electric potential across the electrodes.

U.S. Pat. No. 5,437,999, "Electrochemical Sensor", discloses an electrochemical biosensor test strip with a precisely defined electrode field applying technologies generally used in PCB industries adequately to an electrochemical biosensor test strip. This electrochemical biosensor test strip can operate analysis very precisely with a small amount of samples.

FIG. 1 is a plan view of a conventional electrochemical biosensor test strip. In FIG. 1, 11 is a recognition electrode, 12 a reference electrode, 13 a working electrode and 14 a reaction portion on which a reagent is fixed.

FIG. 2 is a circuit diagram of a conventional electrochemical biosensor readout meter using the test strip 10 shown in FIG. 1, FIG. 3A is a waveform of the working voltage applied to the working electrode 13 by the working voltage generating circuit 21, and FIG. 3B is a waveform of the electric current flowing in the working electrode 13 depending on the introduction of sample.

Below, referring to FIG. 2 and FIG. 3, the operation of a conventional electrochemical biosensor readout meter 20 will be described. When a test strip 10 as shown in FIG. 1 is inserted into the readout meter 20, the voltage of point A changes into 0V from 5V. This change of voltage is recognized by a microprocessor 26 serving as a controller, and the insertion of the test strip can be detected. At this point of detecting the insertion of the test strip (t0), the microprocessor 26 controls a working voltage generating circuit 21 to apply a fixed voltage, for example 300 mV, to a working electrode 13.

When blood and the like is introduced to the reaction part 14(t1), a material to be analyzed from blood reacts with a reagent, generating electric charges. And these electric charges form the electric current by the voltage which has been applied to the working electrode 13. The electric current increases depending on the advance of reaction between the reagent and the material to be analyzed as shown in FIG. 3B. When the current becomes a certain amount(ith)(t2), the microprocessor 26 controls the working voltage generating circuit 21 not to apply any voltage to the working electrode 13. The reason for waiting until the current becomes a certain amount(ith), is to prevent malfunctioning by noise etc.

Since the working voltage is substantially 0V, the electric charges generated by the reaction between the material to be analyzed and the reagent, cannot flow via the working electrode 13, gathering around the working electrode 13. After the working voltage is substantially 0V, at the point t3, the working voltage of 300 mv is applied to the working electrode 13. Here, the time from t2 to t3 is generally called 'incubation time'. The electric charges gathering around the working electrode during incubation time, simultaneously come to flow via the working electrode 13, when the working voltage of 300 mv is applied to the working electrode at t3. Therefore, as shown in FIG. 3B the peak electric current(Ip) emerges at t3.

Referring to the circuit diagram in FIG. 2, the principle of measuring the concentration of a material to be analyzed by measuring the current flowing in the working electrode 13 is described as follows. The current flowing in the working electrode 13 is converted into the voltage by the resistance (R1) which is in feedback-loop of the output terminal and the (−)input terminal of the operational amplifier. This converted voltage is changed into a digital signal by the analogue-digital(A/D) converter 23. The microprocessor 26 has in store the data on the relations of the material to be analyzed from sample to the current. The microprocessor 26 measures the concentration of the material to be analyzed, by reading the current flowing in the working electrode 13 at the time of t4 at which the peak current(Ip) has passed to some degree. The reason for measuring the concentration of the material to be analyzed at t4, is that the value of peak current varies with the state of coupling the reagent to the reference electrode and the working electrode, although the concentration of the material to be analyzed from sample is same.

As described above, so far there was no voltage applied to the working electrode during the incubation time, so that the peak current at t3 was very high. Therefore, if the resistance R1 becomes high, the distortion of signal appears nearby t3 at which the peak current occurs corresponding to the limitation of the operational amplifier OP1, accordingly the current at t4 is also affected. FIG. 4a is the current waveform in case that the resistance R1 is so small that the current flowing in the working electrode can sufficiently flow nearby t3. And FIG. 4b is the current waveform in case that the resistance R1 is so large that the current flowing in the working electrode cannot sufficiently flow nearby t3. In this case, the value of peak current varies with the state of coupling the reagent to the reference electrode and the working electrode so that the current measured at t4 varies with the test strip used. Accordingly, there was the problem of reproduction. Also, if the resistance R1 is decreased so as to let a large peak current flow without distortion, the waste of expenses is occurred since the voltage measured at t4 is relatively much smaller than the voltage at t3 and every bit of A/D converter 23 cannot be used.

Besides, a conventional biosensor readout meter used only one operational amplifier OP1 so as to convert the current flowing in electrodes into the voltage, as shown in FIG. 2. For example, when the reference voltage of the A/D is 3.7V, the value of the resistance R1 100 kΩ and the (+)power supply voltage of the operational amplifier 5V, the current range measurable at t4 is 0<i<37 μA and the maximum value of peak current allowable in the operational amplifier is 50 μA. If the value of peak current is to be raised, the maximum current range measurable at the time of t4 becomes higher than 37 μA. In case the conversion bit of the A/D converter 23 is 8 bit, if the maximum range of current grows larger, the resolution grows worse. Therefore, to gain the preferable resolution the conversion bit should be raised. In such a case, since an expensive A/D converter should be used there was the problem of a rise in expenses.

DISCLOSURE OF THE INVENTION

An object of the present invention is to provide an electrochemical biosensor readout meter which does not cause the distortion of peak current so that the reproducibility is improved.

Also, another object of the present invention is to provide an electrochemical biosensor readout meter with high resolution at low expense.

To achieve the objects as described above, this invention is characterized in a readout meter using the electrochemical biosensor test strip provided with an insulating substrate, a reference electrode and a working electrode formed parallel in a lengthwise direction on the insulating substrate, and a reagent which is fixed over the reference electrode and the working electrode on the insulating substrate, and generates electric charges corresponding to the concentration of a specific material to be analyzed by reacting to this material depending on the insertion of sample, comprising:

a working voltage generating circuit applying a working voltage to the working electrode; a voltage converting device converting the electric current flowing through the working electrode into voltage; an amplifier outputting an analogue voltage signal, amplifying the converted voltage from the voltage converting device; an A/D converter converting the analogue voltage signal from the amplifier into a digital voltage signal; a controller which operates the working voltage generating circuit to apply a first voltage to the working electrode when the test strip is inserted into the readout meter(t0), to apply a second voltage to the working electrode for a fixed period of time after a certain time(t2) when the sample is inserted(t1), then(t3) operates the working voltage generating circuit to apply a third voltage to the working electrode, and measures the concentration of the material to be analyzed by reading the digital voltage signal from the A/D converter after a certain time(t4) from the applying point of the third voltage(t3); wherein the voltage converting device is set to convert the peak in the current generated at the applying point of the third voltage(t3) into the corresponding voltage without distortion, and the amplifier is set to make the digital voltage signal at the measuring point(t4) become below the reference voltage of the A/D converter.

Also, this invention is characterized in a readout meter using the electrochemical biosensor test strip provided with an insulating substrate, a reference electrode and a working electrode formed parallel in a lengthwise direction on the insulating substrate, and a reagent which is fixed over the reference electrode and the working electrode on the insulating substrate, and generates electric charges corresponding to the concentration of a specific material to be analyzed by reacting to this material depending on the insertion of sample, comprising:

a working voltage generating circuit applying a working voltage to the working electrode; a voltage converting device converting the electric current flowing through the working electrode into a analogue voltage signal; an A/D converter converting the analogue voltage signal from the voltage converting device into a digital voltage signal; a controller which operates the working voltage generating circuit to apply a first voltage to the working electrode when the test strip is inserted into the readout meter(t0), to apply a second voltage to the working electrode for a fixed period of time after a certain time(t2) when the sample is inserted (t1), then(t3) operates the working voltage generating circuit to apply a third voltage to the working electrode, and measures the concentration of the material to be analyzed by reading the digital signal from the A/D converter after a certain time(t4) from the applying point of the third voltage (t3); wherein the second voltage is not substantially 0V and smaller than the first voltage.

In accordance with the present invention, it is possible to provide an electrochemical biosensor readout meter with high reproducibility by preventing the distortion of the peak current. Also, it is possible to provide an electrochemical biosensor readout meter with high resolution at low expense.

BRIEF DESCRIPTION OF THE INVENTION

BEST MODES FOR CARRYING OUT THE INVENTION

Hereinafter, an embodiment of the present invention will be described in detail with reference to the accompanying drawings.

Figure 1:
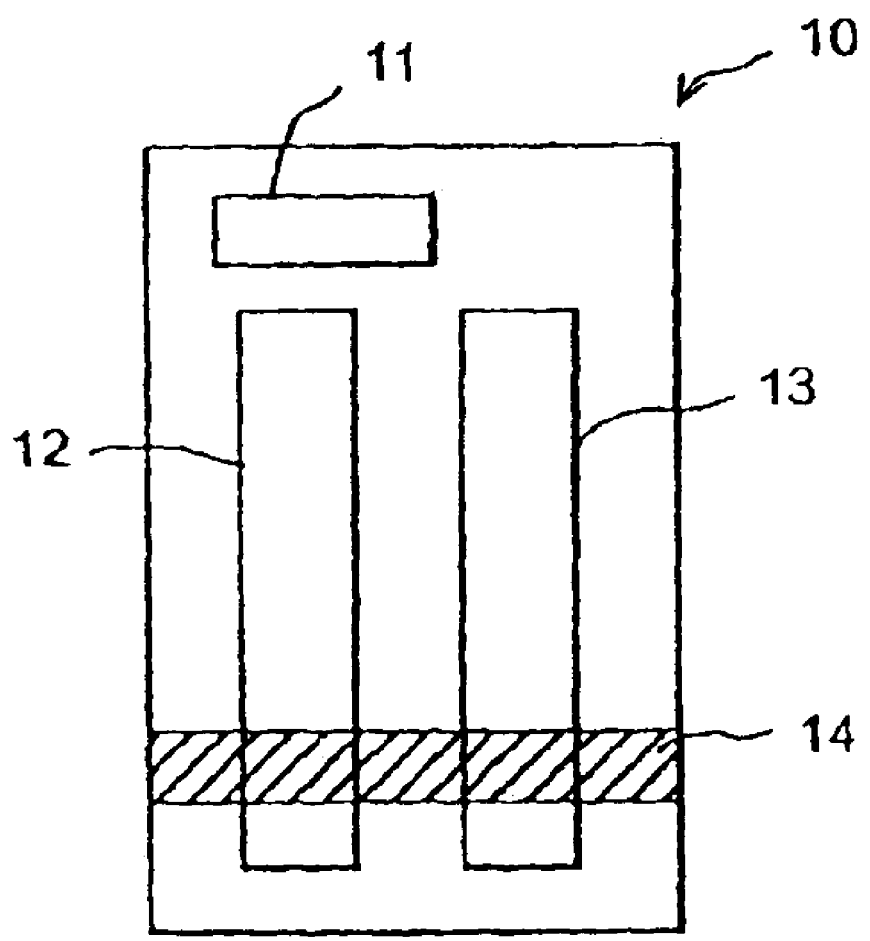
FIG. 1 is a plan view of a conventional electrochemical biosensor test strip.
Figure 2:
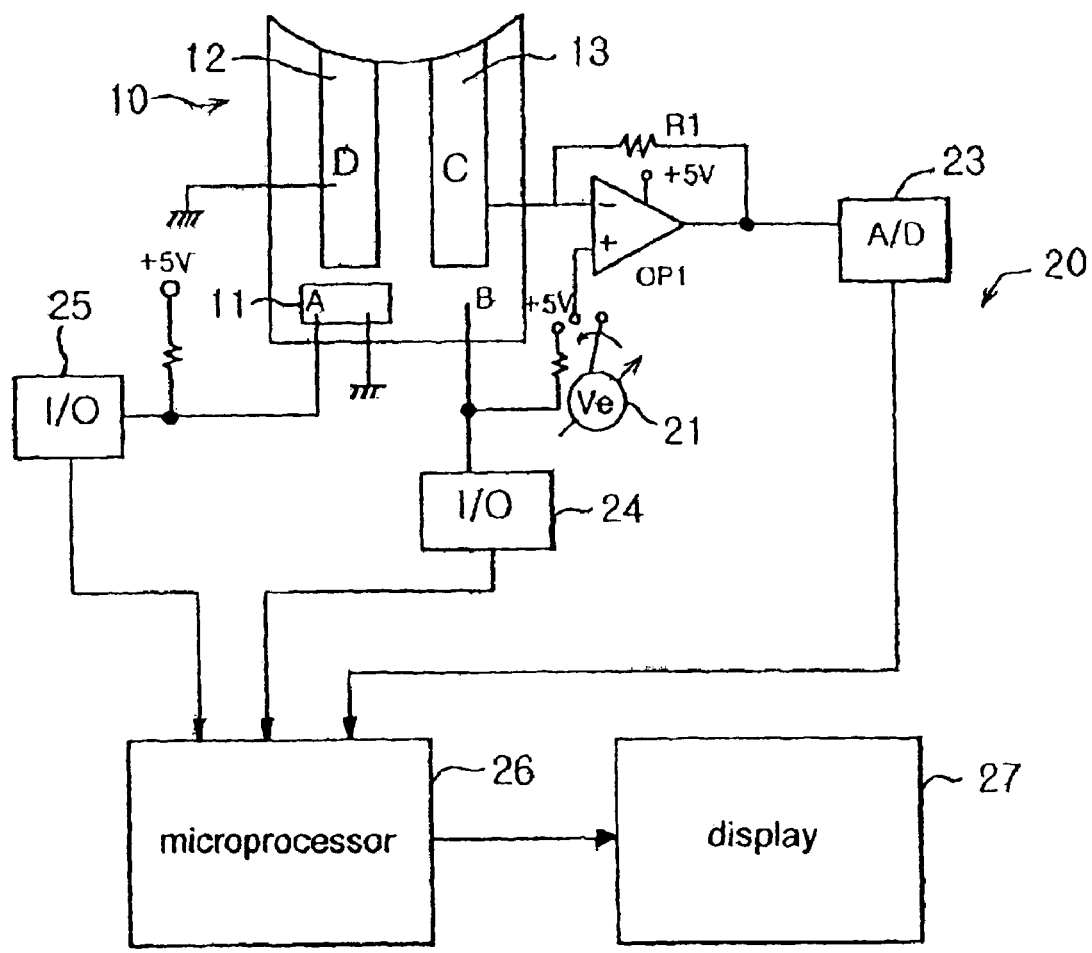
FIG. 2 is a circuit diagram of a conventional electrochemical biosensor readout meter.
Figure 3A:
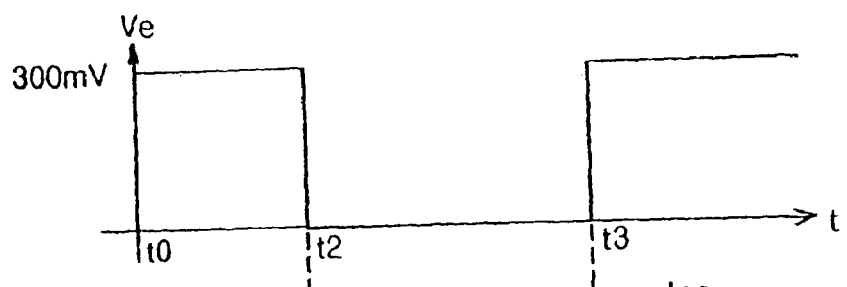
FIG. 3A shows a waveform of a conventional working voltage.
Figure 3B:
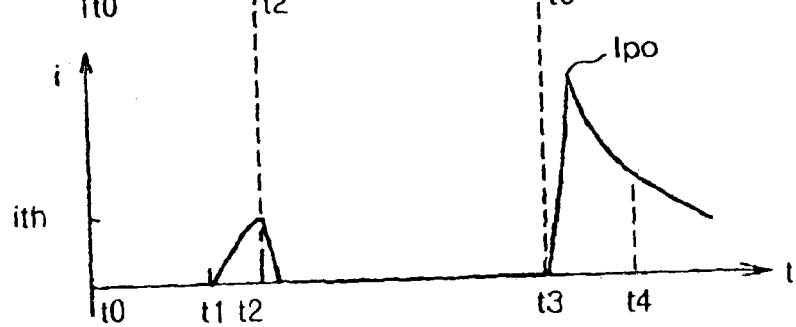
FIG. 3B is a waveform illustrating the current flowing through the working electrode.
Figure 4:
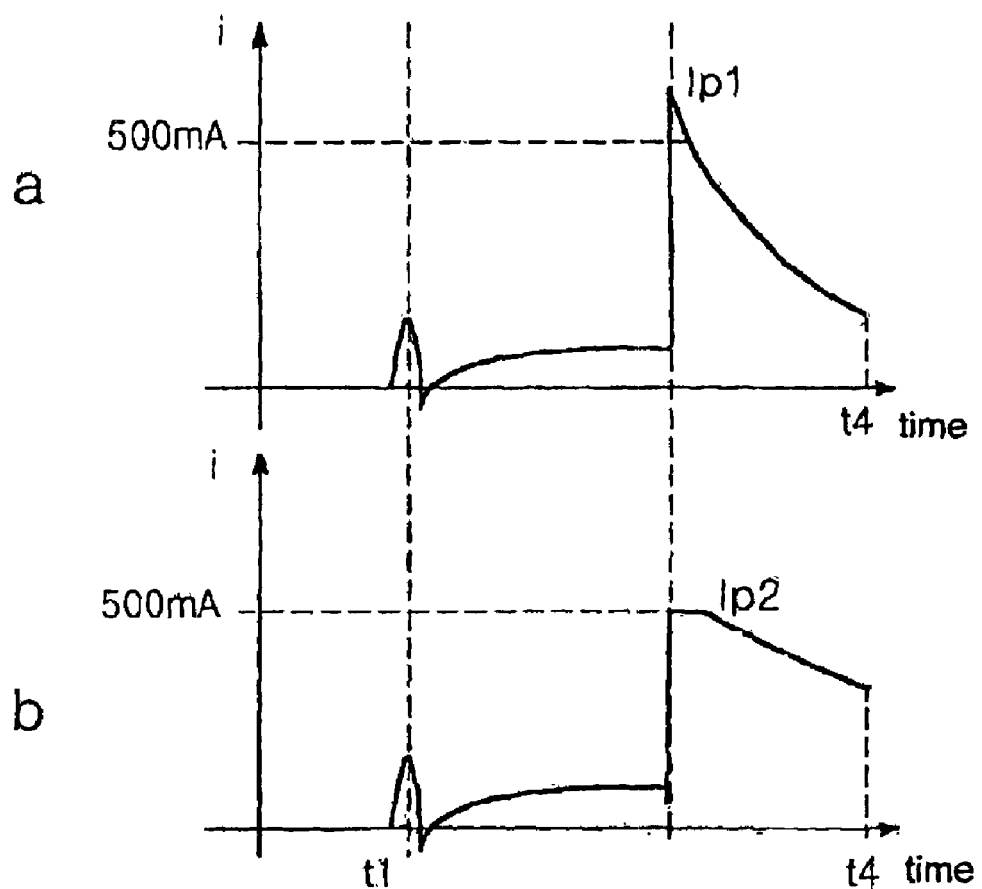
FIG. 4 shows a waveform of the current flowing through the working electrode, illustrated as the peak current distorted.
Figure 5:
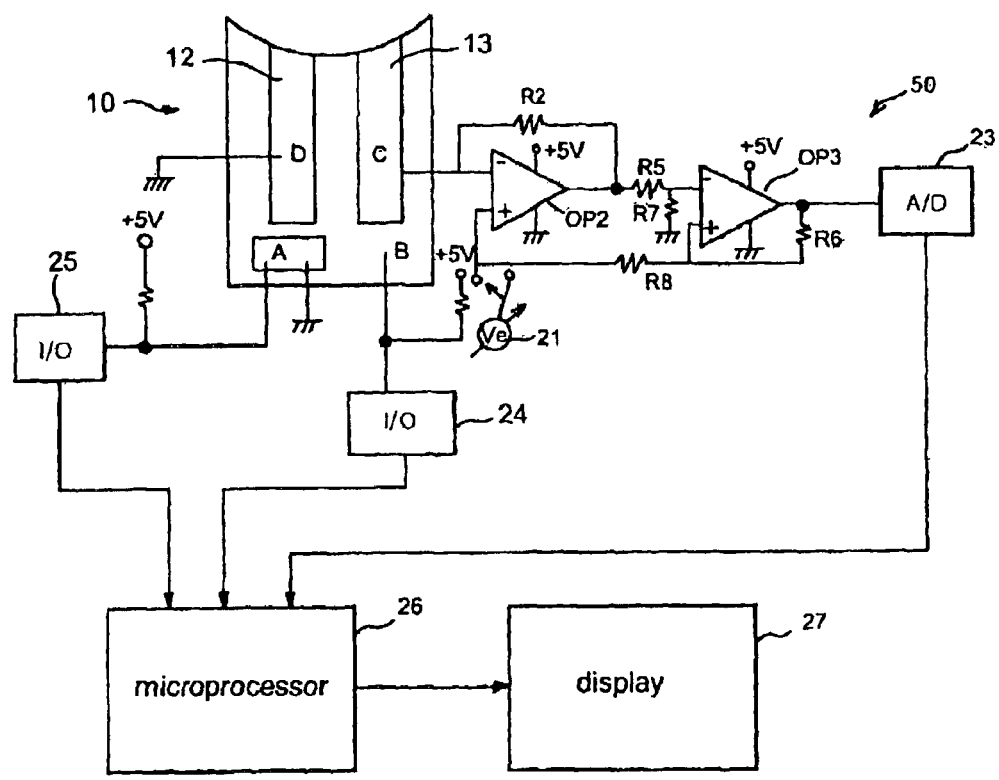
FIG. 5 is a circuit diagram of an electrochemical biosensor readout meter in accordance with an embodiment of the present invention.

FIG. 5 shows a circuit diagram of the electrochemical biosensor readout meter according to this invention. Like reference numerals are used for like components shown in FIG. 2. Compared with the conventional electrochemical biosensor readout meter shown in FIG. 2, the present invention is different in that the operational amplifier converting the current flowing through the working electrode 13 into the voltage, and inputting this voltage to the A/D converter 23, is composed of two stages while the conventional one is composed of one stage.

Figures 6A, 6B:
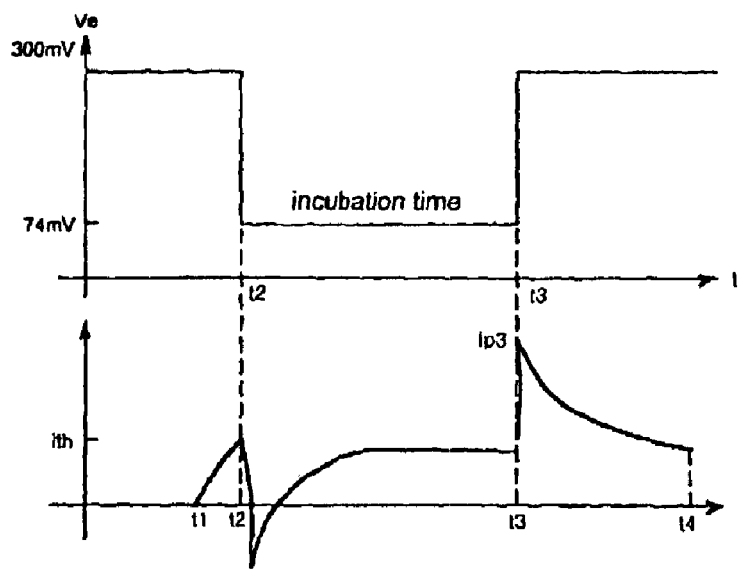
FIG. 6A shows the waveform of the working voltage according to the present invention.
FIG. 6B is a waveform illustrating the current flowing through the working electrode.

FIG. 6A is a waveform of the working voltage applied to the working electrode, and FIG. 6B shows a waveform of the current flowing through the working electrode in accordance with this invention.

Referring to FIG. 5 and FIG. 6, the operation will be described in detail. When the test strip 10 is inserted into the readout meter 50 (t0), the value of point A is turned into 0V from 5V by the recognition electrode 11, and the microprocessor 26 recognizes by the change of voltage whether the test strip 10 is inserted. At this time, as shown in FIG. 6A, the microprocessor 26 operates the voltage generating circuit 43 to apply 300 mV to the working electrode 13. And waits until the blood is inserted into the reaction part 14 of the test strip 10. When the blood is inserted into the reaction part 14 of the test strip 10 (t1), as shown in FIG. 6A, the microprocessor 26 waits till the current flowing in the test strip 10 becomes more than a fixed value (t2), distinguishes the insertion of the blood, and operates the working voltage generating circuit 21 to apply 74 mV, not substantially 0V, as a working voltage to the working electrode 13 of the test strip 10.

In FIG. 5, the first operational amplifier OP2 is to determine the peak current, and the second operational amplifier OP3 is to determine the maximum current which the A/D 23 can measure. When the peak current is called Ip and the voltage applied to the (+)power supply terminal of the operational amplifier OP2 is +5V, Ip is determined as Ip=5/R2. In case R2 is 10KΩ, Ip is 500 $\mu$A. When R5 is set to equal R8 and R6 is R7, the amplification factor of the second operational amplifier OP3 is R6/R8. Therefore, the amplification factor of the current which the A/D converter 23 reads, equals R2R6/R8. Accordingly, when R2 is set to 10 kΩ, R6 470 kΩ, and R8 51 kΩ, the maximum current which can be read at t4 is 3.7/(10 k*470K/51K), that is 40.1 $\mu$A.

If the peak current (Ip) becomes larger, it is practicable to decrease R2 and control the ratio of R6/R8, so that the peak current (Ip) and the maximum current read at t4 can be independently controlled. Therefore, as shown in FIG. 6B, the current waveform of which the peak current is distortionless, can be achieved.

In the present invention, as shown in FIG. 6A, the working voltage of 74 mV was applied, not 0V, for the incubation time. Thereby, the current generated by the chemical reactions is exhausted little by little for the incubation time so that the peak current (IP3) of FIG. 6B becomes smaller than the peak current (IP0) of the time when 0V is applied. Therefore, in case of measuring the same concentration, the peak current is constant. Accordingly, the reproduction can be better as the measurement is repeated because the value measured at t4 becomes constant.

What is claimed is:

1. A readout meter using an electrochemical biosensor test strip provided with an insulating substrate, a reference electrode and a working electrode formed parallel in a lengthwise direction on the insulating substrate, and a reagent which is fixed over the reference electrode and the working electrode on the insulating substrate, and which generates electric charges corresponding to the concentration of a specific material to be analyzed by reacting to this material depending on the insertion of sample into the test strip and the readout meter, comprising:

a working voltage generating circuit applying a working voltage to the working electrode;
   a voltage converting device converting the electric current flowing through the working electrode into voltage;
   an amplifier device outputting an analogue voltage signal, amplifying the converted voltage from the voltage converting device;
   wherein the voltage converting device and amplifier device are provided as separate elements and the voltage converting device includes an operational amplifier;
   an A/D converter converting the analogue voltage signal from the amplifier into a digital voltage signal; and
   a controller which operates the working voltage generating circuit to apply a first voltage to the working electrode when the test strip is inserted into the readout meter (t0), to apply a second voltage to the working electrode for a fixed period of time after a certain time (t2) when the sample is inserted (t1), then (t3) operates the working voltage generating circuit to apply a third voltage to the working electrode, and measures the concentration of the material to be analyzed by reading the digital voltage signal from the A/D converter after a certain time (t4) from the applying point of the third voltage (t3);
   wherein the voltage converting device is set to convert the peak in the current generated at the applying point of the third voltage (t3) into a corresponding voltage without distortion, and the amplifier device is set to make the digital voltage signal at the measuring time (t4) become below the reference voltage of an A/D converter.

2. The readout meter as set forth in claim 1, wherein the third voltage is the same as the first voltage.

3. The readout meter as set forth in claim 2, wherein the second voltage is not substantially 0V and is less than the first voltage.

4. The readout meter as set forth in claim 1, wherein the second voltage is not substantially 0V and is less than the first voltage.

5. A readout meter using an electrochemical biosensor test strip provided with an insulating substrate, a reference electrode and a working electrode formed parallel in a lengthwise direction on the insulating substrate, and a reagent which is fixed over the reference electrode and the working electrode on the insulating substrate, and which generates electric charges corresponding to the concentration of a specific material to be analyzed by reacting to this material depending on the insertion of sample into the test strip and the readout meter, comprising:

a working voltage generating circuit applying a working voltage to the working electrode;
   a voltage converting device converting the electric current flowing through the working electrode into an analogue voltage signal;
   an A/D converter converting the analogue voltage signal from the voltage converting device into a digital voltage signal; and
   a controller which operates the working voltage generating circuit to apply a first voltage to the working electrode when the test strip is inserted into the readout meter (t0), to apply a second voltage to the working electrode for a fixed period of time after a certain time (t2) when the sample is inserted(t1), then (t3) operates the working voltage generating circuit to apply a third voltage to the working electrode, and measures the concentration of the material to be analyzed by reading the digital signal from the A/D converter after a certain time (t4) from the applying point of the third voltage (t3);
   wherein the second voltage is not substantially 0V, and less than the first voltage.

6. The readout meter as set forth in claim 5, wherein the third voltage is the same as the first voltage.

* * * * *